(12) United States Patent
Hall (10) Patent No.: US 8,141,246 B2
(45) Date of Patent: Mar. 27, 2012

(54) METHODS AND DEVICES FOR JOINING CABLES

(75) Inventor: Peter C. Hall, Andover, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 380 days.

(21) Appl. No.: 12/478,448

(22) Filed: Jun. 4, 2009

(65) Prior Publication Data

US 2009/0318999 A1 Dec. 24, 2009

Related U.S. Application Data

(60) Provisional application No. 61/074,304, filed on Jun. 20, 2008.

(51) Int. Cl.
*H01R 43/02* (2006.01)
*A61N 1/04* (2006.01)
*A61N 1/375* (2006.01)

(52) U.S. Cl. ............. 29/866; 29/860; 29/867; 607/122; 607/123; 607/37

(58) Field of Classification Search ............ 29/860–873; 706/37, 115–119, 722
See application file for complete search history.

(56) References Cited

U.S. PATENT DOCUMENTS

| 3,224,916 | A | | 12/1965 | Soloff et al. |
| 3,284,257 | A | | 11/1966 | Soloff et al. |
| 5,676,694 | A | * | 10/1997 | Boser et al. ................... 607/122 |
| 5,789,720 | A | * | 8/1998 | LaGally et al. .......... 219/121.64 |
| 5,861,023 | A | * | 1/1999 | Vachon ......................... 607/121 |
| 5,964,793 | A | * | 10/1999 | Rutten et al. .................. 607/119 |
| 6,141,205 | A | | 10/2000 | Nutzman et al. |
| 6,181,971 | B1 | | 1/2001 | Doan |
| 6,321,114 | B1 | | 11/2001 | Nutzman et al. |
| 6,968,237 | B2 | * | 11/2005 | Doan et al. ..................... 607/122 |
| 7,035,077 | B2 | | 4/2006 | Brendel |
| 7,187,974 | B2 | | 3/2007 | Haeg et al. |
| 7,512,447 | B2 | * | 3/2009 | Marshall et al. .............. 607/122 |
| 8,027,739 | B2 | * | 9/2011 | Hall et al. ...................... 607/121 |
| 2002/0147486 | A1 | * | 10/2002 | Soukup et al. ................ 607/122 |
| 2005/0228469 | A1 | * | 10/2005 | Zarembo et al. .............. 607/122 |
| 2006/0241734 | A1 | * | 10/2006 | Marshall et al. .............. 607/122 |
| 2006/0282144 | A1 | * | 12/2006 | Knapp et al. .................. 607/116 |
| 2008/0294158 | A1 | * | 11/2008 | Pappone et al. ................. 606/41 |
| 2009/0076576 | A1 | * | 3/2009 | Hall et al. ...................... 607/121 |
| 2009/0281607 | A1 | * | 11/2009 | Arnholt ......................... 607/122 |
| 2009/0287285 | A1 | * | 11/2009 | Lynn ............................. 607/126 |
| 2009/0306753 | A1 | * | 12/2009 | Lynn et al. .................... 607/127 |
| 2009/0318999 | A1 | * | 12/2009 | Hall ............................... 607/37 |

* cited by examiner

*Primary Examiner* — Boyer D Ashley
*Assistant Examiner* — Kaying Kue
(74) *Attorney, Agent, or Firm* — Faegre Baker Daniels LLP (57) ABSTRACT

Methods for ultrasonically joining portions of a medical lead are provided. One method includes providing a conductor, a fitting and a coil electrode. The conductor has a distal portion that includes an inner conductive portion and an outer insulative portion. The fitting has a first cavity and a second cavity, the first cavity being sized and configured to receive the distal portion of the conductor and the second cavity being sized and configured to receive a portion of the coil electrode. The conductor is ultrasonically welded within the first opening, providing a mechanical and electrical attachment. The coil electrode is also electrically coupled to the fitting, providing an electrical pathway from the conductor to the coil electrode. Also provided are medical leads including ultrasonic bonds and other methods of ultrasonically joining portions of a medical lead.

15 Claims, 5 Drawing Sheets

METHODS AND DEVICES FOR JOINING CABLES

CROSS-REFERENCE TO RELATED APPLICATION

This application claims the benefit of Provisional Application No. 61/074,304, filed Jun. 20, 2008, entitled "Methods and Devices for Joining Cables," which is herein incorporated by reference in its entirety.

BACKGROUND

Medical leads are used in a wide variety of applications, including the treatment of cardiac conditions. In some applications, cardiac leads have one or more coil electrodes and/or one or more ring electrodes. Electrical conductors are disposed along the cardiac lead to provide an electrical pathway from a proximal portion of the lead to the coil electrodes and/or ring electrodes. There is a need for alternative designs and methods of construction for medical leads.

SUMMARY

In one embodiment of the present invention, a method for mechanically and electrically joining portions of a medical lead comprises providing a fitting defining a first cavity and a second cavity, providing an elongate conductor having a distal portion including an inner conductive member and an outer electrically insulative member, the first cavity sized and configured to receive the distal portion, and providing a coiled conductor having one or more filars having a biocompatible outer surface, the second cavity sized and configured to receive an end portion of the one or more filars. The method further comprises disposing the distal portion of the elongate conductor in the first cavity and disposing the end portion of the one or more filars in the second cavity. The method also includes displacing a portion of the insulative member with ultrasonic energy to electronically couple the fitting and the inner conductive member; and welding at least a part of the distal portion of the elongate conductor to the fitting with ultrasonic energy.

In another embodiment of the present invention, a method for mechanically and electrically joining two portions of a medical lead comprises providing an elongate conductor with a distal portion having an inner electrically conductive member and an outer electrically insulative layer disposed around the inner electrically conductive member and providing an electrode having a biocompatible outer surface. The method further comprises disposing a portion of the electrode adjacent a distal portion of the electrically insulative layer and providing ultrasonic energy to the elongate conductor, displacing a portion of the insulative layer and forming at least a portion of an electrical pathway between the elongate conductor and the electrode.

In another embodiment of the present invention, a medical lead comprises an elongate shaft including an electrode having a coil including one or more filars having a biocompatible outer surface, the shaft further including an elongate conductor having an inner electrically conductive element and an outer electrically insulative element disposed around the electrically conductive element, the elongate conductor extending from a proximal portion of the shaft to a location adjacent the electrode. The lead also includes a fitting defining a first cavity and a second cavity, a distal portion of the elongate conductor disposed in the first cavity, the distal portion including a portion of the conductive element and a portion of the insulative element, the conductive element being welded to the fitting in a weld area. In addition, the one or more filars of the electrode are disposed in the second cavity and electrically coupled to the fitting and the insulative element extends along a portion of the conductive element, into the first cavity and around the weld area.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
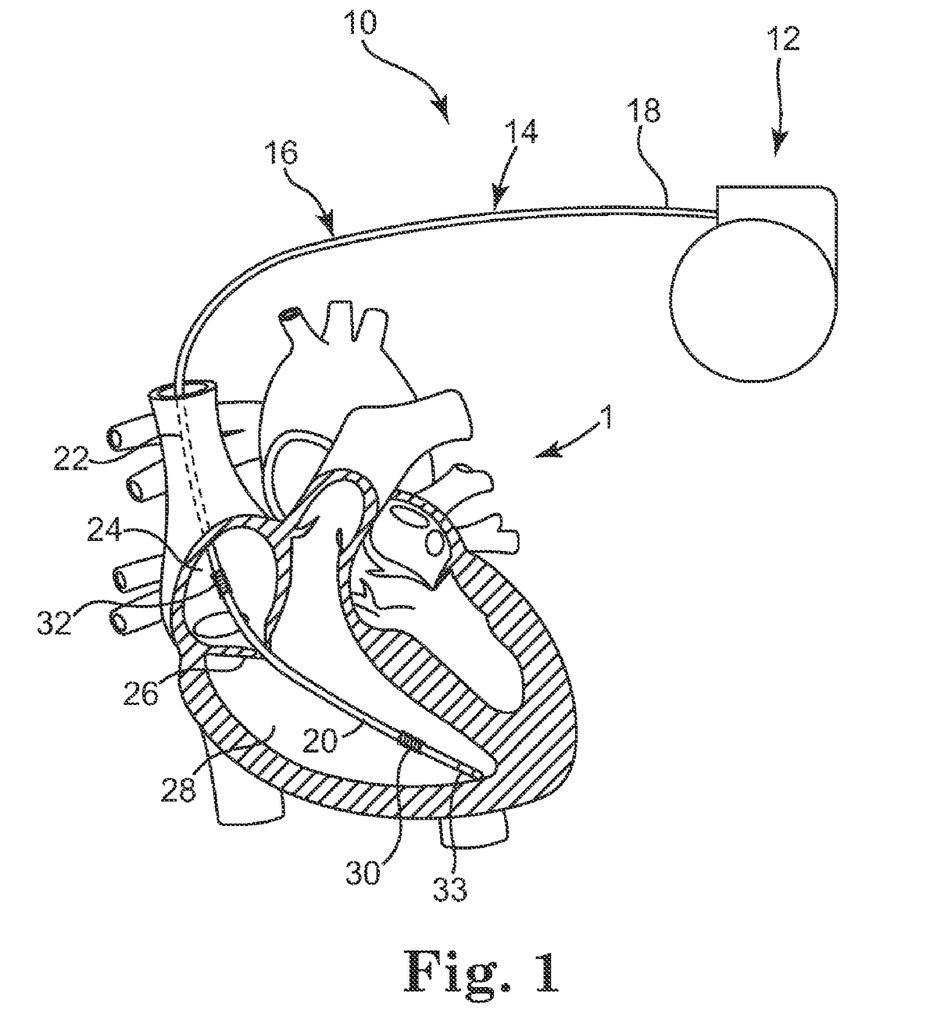
FIG. 1 shows a cut-away view of a human heart together with a cardiac pacing system according to some embodiments of the present invention.

FIG. 1 shows a cut-away view of a human heart 1 together with a cardiac pacing system 10 according to some embodiments of the present invention. The pacing system 10 includes a pulse generator 12 and a lead 14. The lead 14 has an elongate shaft 16 with a proximal portion 18 and a distal portion 20. The shaft 16 extends through the vasculature of a patient through the superior vena cava 22, through the right atrium 24 and the tricuspid valve 26 and into the right ventricle 28 of the heart 1.

The pacing system 10 also has one or more shocking electrodes 30, 32 and, optionally, a pace/sense electrode 33 disposed along the shaft 16. In some embodiments, and as shown in FIG. 1, a distal end of the shaft 16 is attached to a portion of the right ventricle 28. A first, distal shocking electrode 30 is disposed along the shaft 16 in the right ventricle 28 near the distal end of the shaft 16. A second, proximal shocking electrode 32 is disposed proximal of the first shocking electrode 30 along the shaft 16, and is disposed in the right ventricle 28, in the tricuspid valve 26 or, as shown in FIG. 1, in the right atrium 24. In some embodiments, the optional pace/sense electrode 33 is disposed near the distal end of the shaft 16, for example distal of the distal shocking electrode 30.

As shown in FIG. 1, in some embodiments the shocking electrodes 30, 32 are coil electrodes, for example when the lead 14 is a shocking, or tachycardia, lead. In addition, in some embodiments the optional pacing/sensing electrode 33 is a ring electrode that is used for transmitting a pacing signal to the heart and/or to sense an electrical signal of the heart.

Figure 2:
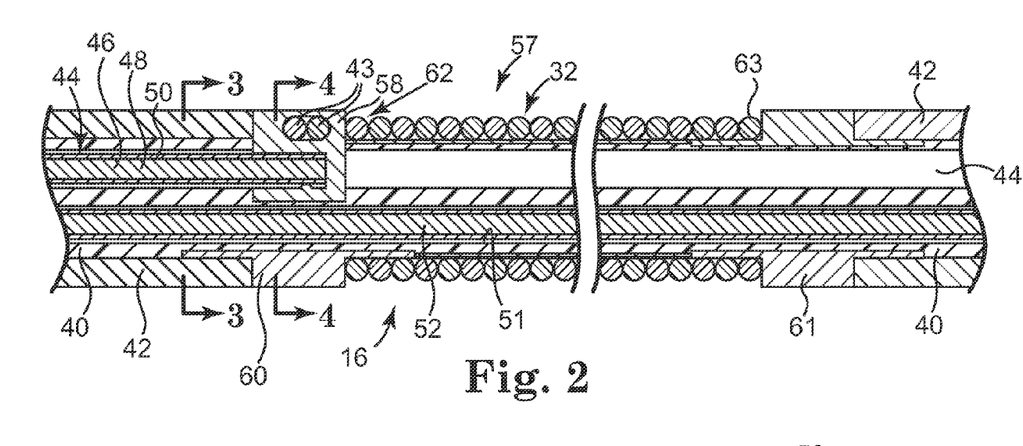
FIG. 2 shows a longitudinal cross-section of a portion of a cardiac lead according to some embodiments of the present invention.
Figure 3:
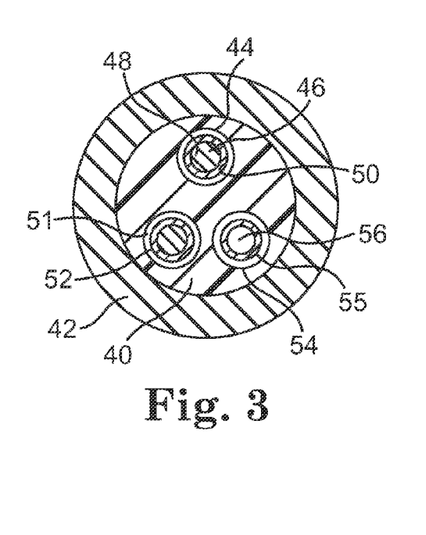
FIG. 3 shows a cross-section of a portion of a cardiac lead according to some embodiments of the present invention.
Figure 4:
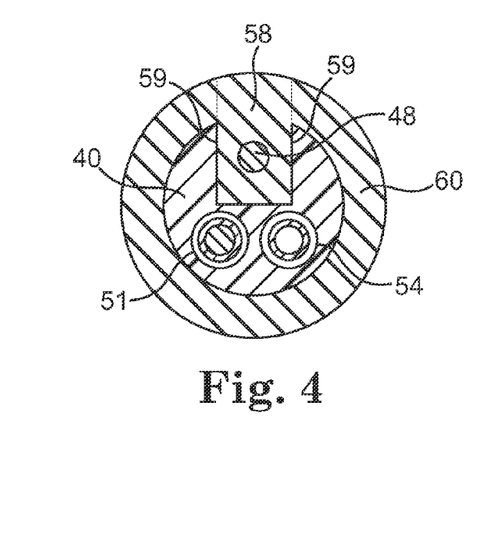
FIG. 4 shows a cross-section of a portion of a cardiac lead according to some embodiments of the present invention.

FIG. 2 shows a longitudinal cross-section of a portion of the lead shaft 16 according to some embodiments of the present invention, and FIGS. 3 and 4 show cross-sections of different portions of the lead shaft 16. The lead shaft 16 has a central body portion 40 and an outer layer 42 disposed around the central body portion 40. The coil electrode 32 is disposed around a portion of the lead shaft 16 and has a number of filars 43.

In some embodiments, and as best shown in FIGS. 3 and 4, the central body portion 40 is a multilumen tubular member 40. The multilumen tubular member 40 comprises medical grade silicone or any other suitable material. In some embodiments, the outer layer 42 comprises a material with increased abrasion resistance relative to the multilumen tubular member 40, for example an abrasion resistant silicone tube that is disposed over the multilumen tubular member 40. In other embodiments, the outer layer 42 has increased or decreased lubricity or other desired characteristics.

As shown best in FIGS. 2 and 3, the multilumen tubular member 40 has a first lumen 44 in which a first conductor 46 is disposed. The first conductor 46 is a cable conductor having an inner conductive member 48 and an insulation layer 50 which electrically isolates the inner conductive member 48 from the surrounding environment. In some embodiments, the conductive member 48 is a solid wire, while in other embodiments the conductive member 48 comprises a number of wires which are braided or otherwise disposed together to form a cable. The wire or wires of the conductive member 48 comprise any suitable material or materials, for example a silver core that is clad with a MP35N (e.g., low Titanium MP35N). The insulation layer 50 comprises any suitable electrically insulative material, for example a layer of electrically insulative polymeric material such as ePTFE.

The multilumen tubular member 40 also has a second lumen 51 with a second conductor 52 disposed therein. In some embodiments, the second conductor 52 is a cable conductor similar to any of the embodiments of the first conductor 46 described above. In addition, the multilumen tubular member 40 has a third lumen 54 that has a third conductor 55 disposed therein. In some embodiments, the third conductor 55 is a coil conductor defining a lumen 56.

Turning again to FIG. 2, an electrode assembly 57 includes the coil electrode 32, a fitting 58, a proximal connector member 60 and a distal connector member 61. The coil electrode 32 has a proximal end 62 and a distal end 63 and the one or more filars 43 are wound in a helical pattern. In some embodiments, the coil electrode 32 has two or more filars 43, three or more filars 43, or four or more filars wound in a helical pattern. For example, as shown in FIG. 2, the coil electrode 32 has two filars that are wound in a side-by-side fashion. In some embodiments, the filars 43 comprise a core of titanium, a layer of tantalum disposed over the titanium core, and a layer of platinum disposed over the tantalum layer. However, other suitable materials or combinations of materials can also be used for the filars 43.

In some embodiments, an electrically active surface of the electrode 32 forms a portion of the outer surface of the shaft 16. In other embodiments, the electrically active surface of the electrode 32 is covered by a protective layer that is permeable to electric current. Such a layer provides a smooth, biocompatible surface around the coil electrode 32 while allowing the flow of electrical current to or from the coil electrode 32. For example, the coil electrode 32 is partially or entirely covered by a microporous ePTFE covering that allows fluids and electrical current to penetrate the covering while blocking the passage of cells through the covering.

The coil electrode proximal end 62 is electrically attached to fitting 58, as described below in more detail. In some embodiments, a notch is made in the multilumen tubular member 40 so that the fitting 58 can be inserted into the multilumen tubular member 40 in alignment with the first conductor 46 in order to facilitate the insertion of the first conductor 46 into a portion of the fitting 58 as discussed below. As shown in FIG. 2, the portion of the first lumen 44 that is distal of the fitting 58 remains open. In other embodiments, the first lumen 44 does not continue distal of the fitting 58 or the first lumen 44 is filled in distal of the fitting 58.

A portion of the coil electrode proximal end 62 is attached to the proximal connector member 60. For example, as shown in FIG. 4, the proximal connector member 60 is a tubular shaped connector member 60 that extends around a portion of the circumference of the lead 16 while leaving a space open for the fitting 58. In some embodiments, the fitting 58 and the proximal connector member 60 are monolithic (they are formed from one piece of material). In other embodiments, the fitting 58 and the proximal connector member 60 are formed from separate pieces of material and may or may not be mechanically connected to one another. For example, in some embodiments the connector member 60 comes into contact with and/or is connected to sides 59 of the fitting 58 along the dashed lines shown in FIG. 4. The coil electrode distal end 63 is attached to the distal connector member 61, which in some embodiments is similar to the proximal connector member 60 except that it is continuous around the circumference of the lead 14. A connection between the coil electrode 32 and the connector members 60, 61 can be formed by welding, soldering, brazing, crimping, staking, adhesive, or by any other suitable method. In other embodiments, the proximal connector member 60 is omitted and the fitting 58 is disposed along the multilumen tubular member 40, for example at the location shown in FIG. 2. Further, in some embodiments the distal connector member 61 is also omitted. In some embodiments in which both of the connector members 60, 61 are omitted, the coil electrode 32 is attached directly to another element of the elongate shaft 16.

In addition, in some embodiments, portions of the lead central body portion 40 and/or the outer layer 42 are mechanically attached to the fitting 58 and/or the connector members 60, 61. For example, as shown in FIG. 2, the lead outer layer 42 extends over a portion of the fitting 58, over a portion of the proximal connector member 61 and over a portion of the distal connector member 61. The lead outer layer 42 is attached to the fitting 58 and the connector members 60, 61 using any suitable method, for example by a friction fit, by heat shrinking the outer layer 42 over the fitting 58 and the connector members 60, 61, or by using an adhesive.

Figure 5:
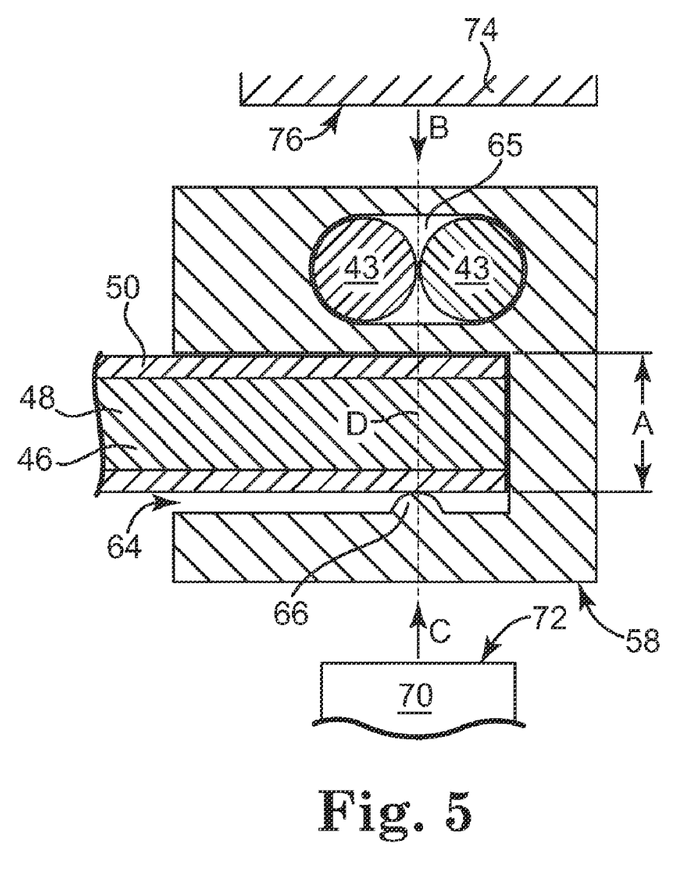
FIG. 5 shows a longitudinal cross section of a fitting for connecting two portions of a medical lead according to some embodiments of the present invention.

FIG. 5 shows a longitudinal cross-section of a fitting 58 for connecting two portions of a medical lead according to some embodiments of the present invention. The fitting 58 comprises Titanium, Platinum, MP35N (e.g., low Titanium MP35N), or other suitable materials, or any combination thereof.

The fitting 58 has a first cavity 64 and a second cavity 65. The first cavity 64 is shaped and configured to receive a distal portion of the first conductor 46, and the first cavity 64 optionally has a protrusion 66 along an inner surface of the cavity 64. A dimension "A" is shown in FIG. 5 and is the narrowest inner dimension of the cavity 64 (including the protrusion 66). In some embodiments, the dimension "A" is approximately the same as, or in some embodiments bigger than, the outer dimension (e.g., the outer diameter) of a distal portion of the first conductor 46, including the thickness of the insulation layer 50. As such, as shown in FIG. 5, a distal portion of the first conductor 46 can be disposed within the cavity 64 without removing any of the insulation layer 50. In addition, the second cavity 65 is shaped and configured to receive one or more filars 43 of the coil electrode 32. For example, two filars 43 are shown disposed in the second cavity 65.

As shown in FIG. 5, in some embodiments of the present invention an ultrasonic welding system is provided. The ultrasonic welding system has a horn 70 with a contact surface 72 and an anvil 74 with a contact surface 76. The horn 70 and the anvil 74 are collectively referred to as the ultrasonic tooling. The horn 70 and anvil 74 are moved in the direction of arrows "B" and "C" in order to bring the surfaces 72, 76 into contact with, and exert pressure on, the fitting 58 (in other embodiments, only the horn 70 is moved and the anvil 74 is held stationary).

Figure 6:
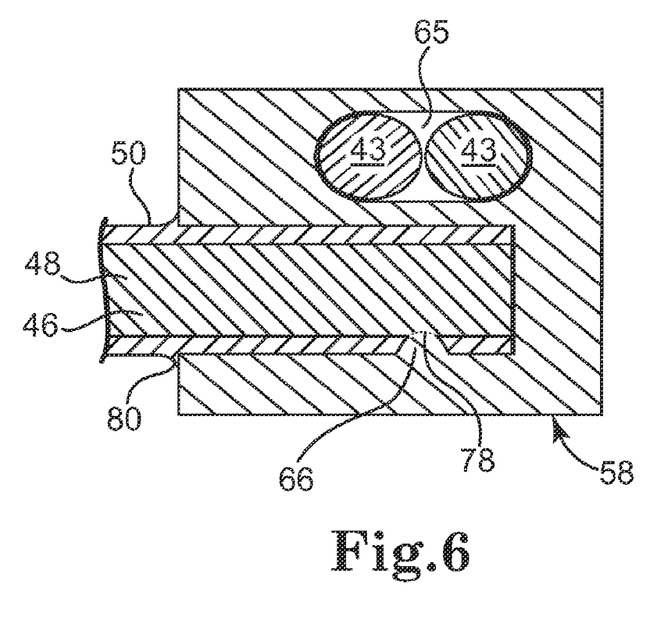
FIG. 6 shows the fitting of FIG. 5 after the fitting has been ultrasonically welded according to some embodiments of the present invention.

FIG. 6 shows the fitting 58 of FIG. 5 after the fitting 58 has been exposed to ultrasonic welding energy from the ultrasonic tooling according to some embodiments of the present invention. In response to the ultrasonic energy, the fitting 58 changes shape and compresses. For example, the dimension "A" of the cavity 64 is narrowed, causing the raised portion 66 to pierce the insulation layer 50 and come into contact with the conductive member 48. In some embodiments, the ultrasonic energy further causes the raised portion 66 to become metallurgically welded to the first conductor 46 at a weld area 78. In other embodiments, the ultrasonic energy deforms the fitting 58 and/or the first conductor 46 to form a mechanical stake or crimp therebetween in the weld area 78. The stake or crimp can be formed in place of, or in addition to, the metallurgical weld.

In one example, a 40 kHz ultrasonic generator having a titanium horn was used to ultrasonically weld a conductor into a fitting. The conductor comprised silver-cored MP35N with an insulation layer and was approximately 0.010 inches in diameter including the insulation (0.007 inches without the insulation). The welding force was approximately 100 pounds (which equated to about 70 ksi) the amplitude was 20 microns, the weld time was 0.27 seconds and the peak energy was 220 Watts. In some embodiments, the welding force that is used is slightly below the yield stress of the fitting. Although this example is included for illustrative purposes, those of ordinary skill in the art would recognize that a variety of ultrasonic welder settings and configurations would be appropriate depending on the materials used, the dimensions of the elements being welded, the condition of the ultrasonic welding equipment, and other factors.

In addition, in some embodiments, as the pressure and ultrasonic energy from the ultrasonic tooling deform and make smaller the cavity 64, the insulation layer 50 is compressed within the cavity 64 and at least a portion of the insulation layer 50 flows from the cavity, forming a seal 80. In some embodiments, the seal 80 and the insulation layer 50 ensures that fluids cannot access the cavity 64, which in some embodiments ensures that the conductive member 48 does not experience significant corrosion or other type of degradation. In some embodiments, the seal 80 is formed and the first conductor 46 and the fitting 58 are ultrasonically welded to one another in a single step.

In some embodiments, the protrusion 66 facilitates the concentration of the ultrasonic energy at a location along the first conductor 46. At least a portion of the protrusion 66 is provided between the anvil 74 and the horn 70. In some embodiments the largest portion of the protrusion 66 (e.g., the location of the smallest dimension "A") is provided at or near the location corresponding to the highest concentration of ultrasonic energy. For example, as shown in FIG. 5, the largest portion of the protrusion 66 and the centerlines of the ultrasonic tooling are aligned along the line "D."

Further, an additional protrusion is optionally provided in the cavity 64 opposite the protrusion 66 in order to provide a further concentration of ultrasonic energy. In addition to, or as an alternative to the one or more protrusions in the cavity 64, in some embodiments the horn 70 and/or anvil 74 have a protrusion or raised portion which provides a concentration of ultrasonic energy and/or a protrusion or raised portion is provided on the top and/or bottom surfaces of the fitting 58. The protrusions can have a variety of geometric shapes. For example, the protrusions can be a pointed protrusion, or the protrusion can be a gentle rise in the surface of the cavity 64, the horn 70, the anvil 74, the top of the fitting 58 and/or the bottom of the fitting 58. In some embodiments, the shape of the protrusion 66 also facilitates the flow of the insulation layer 50 within and from the cavity 64 to form the seal 80. Further, in embodiments with no protrusion 66, the ultrasonic energy may also facilitate the flow of the insulation layer 50 within and from the cavity 64 to form the seal 80 (for example by deforming the cavity 64).

In some embodiments, the ultrasonic energy is provided after both the first conductor 46 is placed in the first cavity 64 and the one or more filars 43 are placed in the second cavity 65, as shown in FIG. 5.

In other embodiments, the ultrasonic energy is provided when the first conductor 46 is disposed in the first cavity 64 in order to provide a metallurgical weld (and/or mechanical stake or crimp) between the fitting 58 and the first conductor 46. The filars 43 are subsequently placed in the second cavity 65 and attached to the fitting 58. In some such embodiments, the filars 43 are attached to the fitting 58 by welding (ultrasonic or other types of welding), soldering, brazing, crimping, staking or other suitable methods.

In addition, when the fitting 58 is exposed to ultrasonic energy, the second cavity 65 may change shape in response to the ultrasonic energy. In some such embodiments, if the ultrasonic energy is provided prior to placing the filars 43 in the second cavity 65, the second cavity 65 is originally sized and configured such that, after the ultrasonic energy changes the shape and/or size of the second cavity 65, the second cavity 65 is sized and configured to receive the filars 43. In other embodiments, the second cavity 65 is not placed in alignment with the ultrasonic tooling such that the ultrasonic energy will not significantly deform the second cavity 65.

As shown best in the combination of FIGS. 2 and 4, the first cavity 64 in the fitting 58 is a bore-shaped cavity that is open at one end. In other embodiments, the cavity extends through the fitting 58, forming two open ends. In some such embodiments, a seal 80 is formed around both open ends, and an insulation material is provided over the distal end of the first conductor 46.

Further, as mentioned above, the ultrasonic energy is directed at the fitting 58 from the top and bottom of the fitting 58, along the line "D" shown in FIG. 5. In other embodiments, the ultrasonic energy is directed at the fitting 58 from other directions. For example, in some embodiments the ultrasonic tooling 70, 74 is configured to make contact with the sides 59 (see FIG. 4) of the fitting 58. In some such embodiments, the protrusions described above are aligned with the delivery of the ultrasonic energy, as described above with respect to FIG. 5. In some embodiments, providing ultrasonic energy from the sides 59 of the fitting 58 facilitates the welding of the first conductor 46 to the fitting 58 without significantly deforming the shape and/or size of the second cavity 65.

In other embodiments, the portion of the fitting 58 that defines the cavity 64 is C-shaped (for example, as shown in cross-section in FIGS. 2, 5 and 6) and the cavity 64 is open on three sides. In some such embodiments, the C-shape is compressed by the application of pressure and ultrasonic energy, simultaneously forming a metallurgical weld (and/or a stake or crimp) between the first conductor 46 and the fitting 58 and deforming the insulation layer 50 to form a seal around the first conductor 46.

Figure 7:
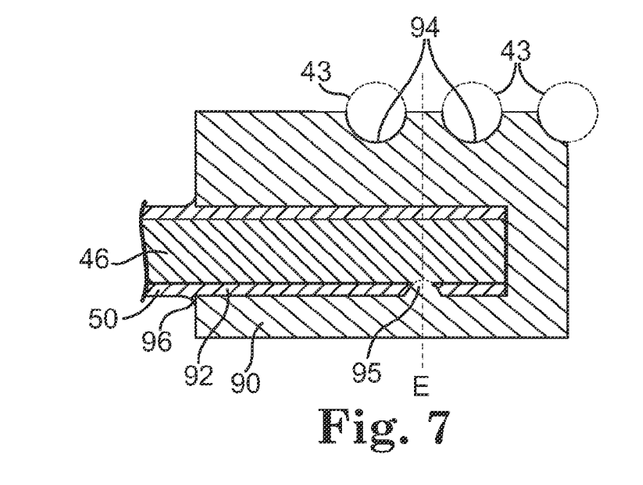
FIG. 7 shows a longitudinal cross-section of a fitting for connecting two portions of a medical lead according to some embodiments of the present invention.

FIG. 7 shows a fitting 90 for connecting two portions of a medical lead according to some embodiments of the present invention. The fitting 90 comprises materials similar to the fitting 58 described above. The fitting 90 has a first cavity 92 and one or more second cavities 94. The first cavity 92 can be similar in size and configuration to any of the embodiments of the first cavity 64 described above. The one or more second cavities 94 are one or more depressions or grooves 94, and are shaped and configured to accommodate the filars 43 (shown in phantom in FIG. 7) of the coil electrode 32.

Similar to the cavity 64, the cavity 92 optionally has a protrusion or raised portion 95 formed therein, similar to the protrusion 66 described above. In some embodiments the protrusion 95 facilitates the concentration of ultrasonic energy, which in turn facilitates the formation of a metallurgical weld (and/or stake or crimp) between the fitting 90 and the first conductor 46. In some embodiments the protrusion 95 facilitates the flow of insulation material to form a seal 96 around the entrance to the cavity 92.

As discussed above with respect to the first cavity 64, the original size of the cavity 92 (before being exposed to ultrasonic energy) is sized and configured to accommodate a distal portion of the first conductor 46, including the insulation layer 50. For example, the narrowest portion of the cavity 92 (e.g., the portion corresponding to the largest portion of the protrusion 95) has a dimension that is sufficiently large to accommodate the distal portion of the first conductor 46 with the insulation layer 50 disposed thereon.

Also, as noted above with respect to the protrusion 66, in some embodiments the protrusion 95 is a sharpened protrusion, or the protrusion or raised portion 95 can have other suitable shapes such as a gentle narrowing of the cavity 92. In some embodiments, the protrusion 95 is centered along a line "E", which is also aligned with a portion of the fitting 90 between the cavities 94. In some embodiments, aligning the ultrasonic tooling (not shown in FIG. 7) along this line "E" facilitates the concentration of ultrasonic energy on the portions of the fitting 90 and the first conductor 46 that are located around the narrowest portion of the cavity 92 (e.g., the center of the protrusion 95 and/or the largest portion of the protrusion 95).

Additionally, a second protrusion is optionally disposed in the cavity 92, for example on an opposite side of the cavity 92 relative to the protrusion 95. As mentioned above with respect to cavity 64, in addition to, or in place of, the one or more protrusions disposed inside the cavity 92, in some embodiments a protrusion or raised portion is disposed on an outside surface of the fitting 90, or on one or more surfaces of the ultrasonic tooling. In some embodiments, the cavity 92 is formed as a bore in the fitting 90 with a single opening. In other embodiments, the cavity 92 extends through the fitting 90, forming two openings, or, as described above with respect to cavity 64, the fitting 90 has a C-shaped cross-section and the cavity 90 is open on three sides.

Further, as mentioned above with respect to the fitting 58, a number of different methods can be used to join together the fitting 90 with the first conductor 46 and the one or more filars 43. For example, the first conductor 46 is disposed in the cavity 92 and the fitting 90 and the first conductor 46 are ultrasonically welded together (from one of a number of different directions, as discussed above). The filars 43 (as shown in phantom in FIG. 7) are then placed in the cavities 94 and the filars 43 are attached to the fitting 90 using any of the methods mentioned above. In another embodiment, the first conductor 46 is disposed in the cavity 92 and the filars 43 are disposed in the cavities 94 and the first conductor 46, the filars 43 and the fitting 90 are ultrasonically welded together in a single step.

Figure 8:
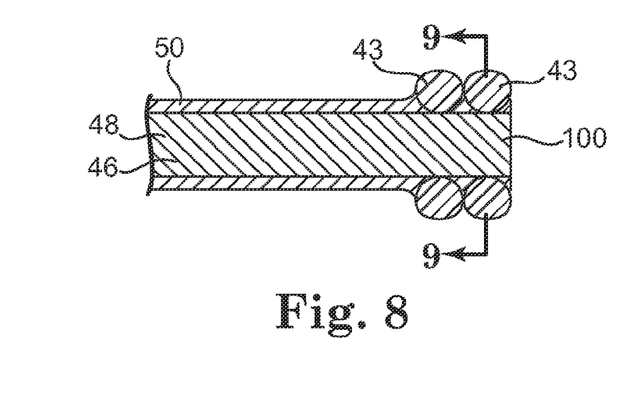
FIG. 8 shows a longitudinal cross-section of a lap joint between two portions of a medical lead according to some embodiments of the present invention.
Figure 9:
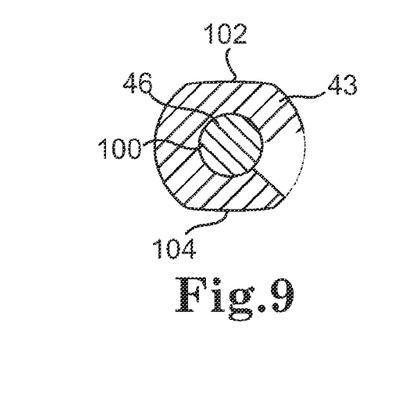
FIG. 9 shows a cross-section of the lap joint of FIG. 8 according to some embodiments of the present invention.

FIG. 8 shows a longitudinal cross-section of a lap joint between two portions of a medical lead according to some embodiments of the present invention and FIG. 9 shows a cross-section of this lap joint. The first conductor 46 has a distal end 100. At or adjacent to the distal end 100, one or more filars 43 are disposed on the first conductor 46. As shown in FIG. 9, in some embodiments the filars 43 are wrapped around a portion of the first conductor 46 approximately one revolution. In other embodiments, the filars 43 are wrapped around the first conductor 46 more than one time, for example two or more, or three or more times. The filars 43 are exposed to ultrasonic energy, forming a metallurgical weld (and/or stake or crimp) between the first conductor 46 and the filars 43. In some embodiments, as shown in FIGS. 8 and 9, the ultrasonic energy deforms the filars 43, forming flattened portions 102, 104 of the filars 43.

In some embodiments, the filars 43 are disposed on the first conductor 46 over the insulation layer 50. Applying pressure and ultrasonic energy to the filars 43 and the first conductor 46 causes the insulation layer 50 to flow away from the interface between the filars 43 and first conductor 46. The application of pressure and ultrasonic energy further causes the filars come into contact with the conductive member 48 of the first conductor 46 and form a metallurgical bond therebetween. Further, in some embodiments the conductive member distal end surface 100 is exposed (uncovered by electrical insulation). In some such embodiments, the distal end surface 100 is separately coated or covered with an electrically insulative material to ensure that electrical signals transmitted along the first conductor 46 efficiently pass to or from the filars 43.

Figure 10:
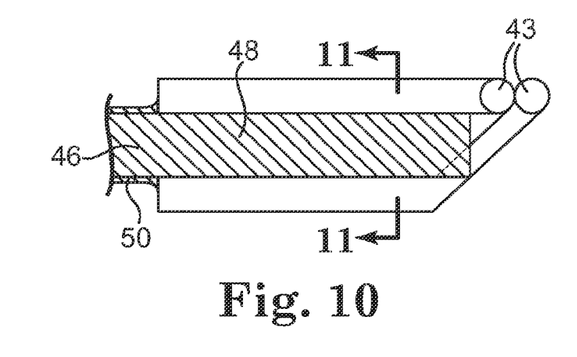
FIG. 10 shows a longitudinal cross-section of a lap joint between two portions of a medical lead according to some embodiments of the present invention.
Figure 11:
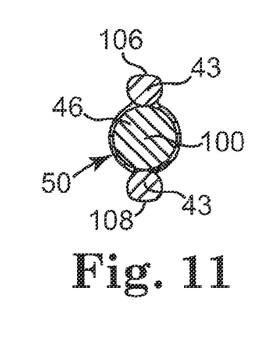
FIG. 11 shows a cross-section of the lap joint of FIG. 10 according to some embodiments of the present invention.

FIG. 10 shows a longitudinal cross-section of a lap joint between two portions of a medical lead according to some embodiments of the present invention and FIG. 11 shows a cross section of this lap joint. A proximal portion of the filars 43 extend longitudinally along the first conductor 46 and a metallurgical bond is formed along at least a portion of the interface between the filars 43 and the first conductor 46.

As shown in FIG. 11, a first filar 43 is disposed on one side of the first conductor 46 and a second filar 43 is disposed on a second side (e.g., an opposite side as shown in FIG. 11) of the first conductor 46. In some embodiments, these filars 43 are disposed along a portion of the first conductor 46 over the insulation layer 50. The filars 43 and the first conductor 46 are exposed to ultrasonic energy, which displaces the insulation layer 50 and allows the filars 43 to come into contact with, and form a metallurgical bond with, the conductive member 48 of the first conductor 46. In some embodiments the ultrasonic energy forms flattened surfaces 106, 108 on the filars 43. Also, in some embodiments an insulative material is disposed over the conductive member distal end surface 100 to ensure that electrical signals transmitted along the first conductor 46 efficiently pass to or from the filars 43.

Figure 12:
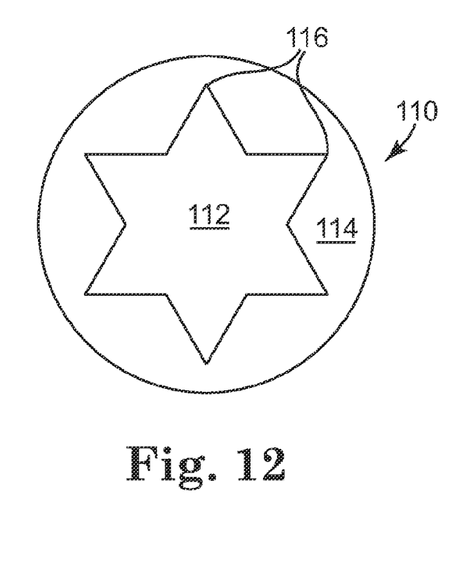
FIG. 12 shows a cross-section of a conductor of a medical lead according to some embodiments of the present invention.

In addition to, or instead of, the protrusions or raised portions on the fittings or the tooling as described above, the conductors of described above also optionally have protrusions or raised portions. For example, FIG. 12 shows a cross-section of a conductor 110 of a medical lead according to some embodiments of the present invention. The cross-section has an inner conductive member 112 and an insulation layer 114. The cross section of the inner conductive member 112 has protrusions or raised portions 116 formed thereon, for example in a star pattern shown in FIG. 12. When disposed adjacent a fitting or a filar, the protrusions 116 facilitate the concentration of ultrasonic energy, which in turn facilitates displacement of the insulation layer 114 and the formation of a metallurgical bond between the conductor 110 and the fitting or the filar. In some embodiments, any of the conductors (e.g., the first conductor 46) discussed herein have inner conductive members 112 with raised portions 116.

In some embodiments, all or a portion of the filars 43 have a cross-section with raised portions. For example, the outer surface of the filars 43 has the cross-sectional shape of the inner conductive member 112, facilitating the concentration of ultrasonic energy at the raised portions 116.

In addition, in order to facilitate the concentration of ultrasonic energy, the conductors or filars optionally have one or more raised portions or protrusions formed along the conductor or filar, for example similar to the raised portions or protrusions discussed above with respect to fittings 58, 90.

As mentioned above, the lead 14 defines multiple lumens 44, 51, 54 and a conductor is disposed in each of the lumens 44, 51, 54. As shown in FIG. 2, the second conductor 52 extends distally of the coil electrode 32 through the second lumen 51, for example to the distal coil electrode 30 (shown in FIG. 1). In some embodiments, the second conductor 52 is electrically coupled to the distal coil electrode 30 using any of the fittings and/or methods described above.

Further, in some embodiments other electrical connections can also be made using the ultrasonic welding methods described herein. For example, in some embodiments the coil conductor 55 (shown in FIGS. 3 and 4) has insulation disposed thereon, and extends distally through the third lumen 54 to the ring electrode 33 (shown in FIG. 1). A portion of the insulated coil conductor 55 is disposed adjacent an electrically conductive surface of the ring electrode 33 and ultrasonic energy is applied to the combination of the coil conductor 55 and the ring electrode 33, displacing the insulation on the coil conductor 55 and forming a metallurgical weld (and/or stake or crimp) between the ring electrode 33 and a portion of the coil conductor 55.

In some embodiments, the ultrasonic welding methods described herein lead to a stronger, more durable metallurgical bond between the two metals being joined when compared to heat welding (e.g., resistance welding) or mechanically joining the metals (e.g., crimping or staking). For instance, when joining metals such as titanium or titanium alloys with nickel, iron, platinum or tantalum, or alloys of these metals, ultrasonic welding provides for a stronger weld compared to heat welding. In some embodiments, a fitting comprising titanium, MP35N or platinum is coupled to a conductor comprising MP35N and silver or a conductor comprising platinum and tantalum.

In addition, with some of the ultrasonic welding methods discussed above, a metallurgical weld (and/or stake or crimp) is formed with an insulated conductor without having to first remove a portion of the insulation. In some embodiments this saves time, reduces complexity in the manufacturing process, and reduces waste.

Further, when the insulation is displaced during the welding methods discussed herein, in some embodiments a portion of the insulation displaces to form a seal. Because the seal is formed from a portion of the insulation of a conductor, the seal and the insulation are a continuous electrical insulation layer along the first conductor. In some embodiments, this seal prevents fluids from accessing the conductive portion of the conductor member. In some such embodiments, the seal is formed during the ultrasonic welding step rather than requiring a separate step to add an electrical seal material such as medical adhesive, saving time, reducing complexity in the manufacturing process, and reducing waste.

Some of the examples that are discussed above are specifically referred to as cardiac leads. However, it is also contemplated that any of the leads or methods of manufacturing leads discussed herein are also suitable for other types of leads, for example neurological leads.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A method for mechanically and electrically joining portions of a medical lead comprising:
    providing a fitting defining a first cavity and a second cavity;
    providing an elongate conductor having a distal portion including an inner conductive member and an outer electrically insulative member, the first cavity sized and configured to receive the distal portion;
    disposing the distal portion of the elongate conductor in the first cavity;
    providing a coiled conductor having one or more filars having a biocompatible outer surface, the second cavity sized and configured to receive an end portion of the one or more filars;
    disposing the end portion of the one or more filars in the second cavity;
    displacing a portion of the insulative member with ultrasonic energy to electronically couple the fitting and the inner conductive member; and
    welding at least a part of the distal portion of the elongate conductor to the fitting with ultrasonic energy.

2. The method of claim 1, including welding the end portion of the one or more filars to the second cavity using ultrasonic energy.

3. The method of claim 2, wherein welding the end portion of the one or more filars to the second cavity using ultrasonic energy is performed at the same time as displacing a portion of the insulative member with ultrasonic energy to electrically couple the fitting and the inner conductive member, which is performed at the same time as welding at least a part of the distal portion of the elongate conductor to the fitting with ultrasonic energy.

4. The method of claim 1, wherein a portion of the insulative member is displaced from the first cavity, forming an electrical seal at an opening of the first cavity.

5. The method of claim 1, wherein the first cavity is a bore in the fitting.

6. The method of claim 1, wherein the second cavity is a depression or groove.

7. The method of claim 1, wherein the first cavity has a protrusion formed therein and welding at least a part of the distal portion of the elongate conductor to the fitting with ultrasonic energy includes welding a portion of the protrusion to the elongate conductor.

8. A method for mechanically and electrically joining two portions of a medical lead comprising:
   providing an elongate conductor with a distal portion having an inner electrically conductive member and an outer electrically insulative layer disposed around the inner electrically conductive member;
   providing an electrode having a biocompatible outer surface;
   disposing a portion of the electrode adjacent a distal portion of the electrically insulative layer; and
   providing ultrasonic energy to the elongate conductor, displacing a portion of the insulative layer and forming at least a portion of an electrical pathway between the elongate conductor and the electrode.

9. The method of claim 8, wherein placing a portion of the electrode adjacent a distal portion of the electrically insulative layer comprises placing a portion the electrically conductive portion of the electrode directly on a distal portion of the electrically insulative layer and wherein providing ultrasonic energy to the elongate conductor includes simultaneously providing ultrasonic energy to the elongate conductor and the electrode.

10. The method of claim 9, wherein disposing a portion of the electrode adjacent a distal portion of the electrically insulative layer includes disposing the electrode around the electrically insulative layer.

11. The method of claim 8, further comprising:
   providing a fitting, the fitting defining a first cavity sized to receive the distal portion of the elongate conductor and a second cavity sized to receive a portion of the electrode;
   disposing the distal portion of the elongate conductor in the first cavity; and
   disposing a portion of the electrode in the second cavity;
   wherein providing ultrasonic energy to the elongate conductor, displacing a portion of the insulative layer and forming a portion of an electrical pathway between the elongate conductor and the electrode includes providing ultrasonic energy to the elongate conductor and the fitting, displacing a portion of the outer electrically insulative portion and electrically coupling the fitting and the elongate conductor.

12. The method of claim 11, wherein forming an electrical pathway between the elongate conductor and the electrically conductive portion of the electrode further includes electrically coupling the fitting and the electrode.

13. The method of claim 11, wherein the elongate conductor is ultrasonically welded with the fitting and the electrode is ultrasonically welded with the fitting in the same step.

14. The method of claim 11, wherein the first cavity is a bore-shaped cavity.

15. The method of claim 11, wherein the second cavity is a groove or depression formed on a surface of the fitting.

* * * * *